US012564428B2

(12) United States Patent
Stauch

(10) Patent No.: US 12,564,428 B2
(45) Date of Patent: Mar. 3, 2026

(54) INTRAMEDULLARY NAIL FOR TRANSVERSE DISTRACTION

(71) Applicant: Roman Stauch, Assamstadt (DE)

(72) Inventor: Roman Stauch, Assamstadt (DE)

( * ) Notice: Subject to any disclaimer, the term of this patent is extended or adjusted under 35 U.S.C. 154(b) by 114 days.

(21) Appl. No.: 18/290,269

(22) PCT Filed: May 9, 2022

(86) PCT No.: PCT/EP2022/062440
§ 371 (c)(1),
(2) Date: Nov. 10, 2023

(87) PCT Pub. No.: WO2022/238303
PCT Pub. Date: Nov. 17, 2022

(65) Prior Publication Data
US 2024/0238018 A1     Jul. 18, 2024

(30) Foreign Application Priority Data

May 12, 2021     (DE) ..................... 10 2021 112 429.8

(51) Int. Cl.
*A61B 17/72*     (2006.01)
*A61B 17/68*     (2006.01)
(52) U.S. Cl.
CPC ...... *A61B 17/7216* (2013.01); *A61B 17/7258* (2013.01); *A61B 2017/681* (2013.01)
(58) Field of Classification Search
CPC ............ A61B 17/7258; A61B 17/7216; A61B 2017/681
See application file for complete search history.

(56) References Cited

U.S. PATENT DOCUMENTS 4,237,875 A     12/1980  Termanini
9,155,574 B2 *  10/2015  Saravia .............. A61B 17/1725
(Continued)

FOREIGN PATENT DOCUMENTS

FR          2 653 006 A1     4/1991
WO       2013023898 A1     2/2013

OTHER PUBLICATIONS

PCT International Application No. PCT/EP2022/062440. International Search Report. Date: Sep. 13, 2022 (3 pages).

*Primary Examiner* — Sameh R Boles
(74) *Attorney, Agent, or Firm* — Jansson Munger & McKinley Ltd.

(57)     ABSTRACT

The invention relates to an intramedullary nail (1) for transverse distraction of a tubular bone (2), the intramedullary nail (1) comprising an at least partially hollow tube body (3) extending in an axial direction of the intramedullary nail (1), at least one locking means for locking the tube body (3) in an end portion of the tubular bone (2), a first inner part (5) and a second inner part (7), which are each arranged within the tube body (3) so as to be displaceable in the axial direction toward each other or with each other, a drive within the tube body (3) for axial displacement of the first inner part (5) relative to the second inner part (7), at least one longitudinal recess (11) in the tube body (3), and at least one lever mechanism (20) which comprises at least one lever element (9, 23, 24) which is designed to be extended out of, and to be retracted again into, the tube body (3) in a radial direction, wherein the displacement of the first inner part (5) relative to the second inner part (7) causes the at least one lever element (9) to be moved or extended out of the at least one lateral longitudinal recess (11) in the tube body (3) or causes the at least one lever element (9) to be
(Continued)

moved or retracted into the at least one lateral longitudinal recess (11) in the tube body (3).

13 Claims, 5 Drawing Sheets

(56)                    References Cited

U.S. PATENT DOCUMENTS

| 11,109,897 | B2 * | 9/2021 | Suddaby ............ A61B 17/1617 |
|---|---|---|---|
| 2005/0124999 | A1 | 6/2005 | Teitelbaum et al. |
| 2005/0182405 | A1 | 8/2005 | Orbay et al. |
| 2013/0296861 | A1 | 11/2013 | Tontz |
| 2014/0222094 | A1 | 8/2014 | Militz et al. |
| 2015/0133937 | A1 | 5/2015 | Benedict |
| 2017/0143387 | A1 | 5/2017 | Jansen |

* cited by examiner

INTRAMEDULLARY NAIL FOR TRANSVERSE DISTRACTION

FIELD OF THE INVENTION

The present invention relates to an intramedullary medical nail for transverse distraction of a tubular bone, and in particular, to a fully implantable, active intramedullary medical nail.

PRIOR ART

A large number of patients with a diabetic background have the problem of insufficient blood circulation to the extremities, especially in the region of the lower legs. In critical cases, a negative course of the disease may lead to amputation. Various approaches to this problem in the field of extremity correction have been developed in orthopaedics, including the finding in some cases that transverse distraction of a tubular bone significantly improves the blood circulation to the corresponding extremity and can thus prevent amputation. In medical literature, this connection is described, for example, in Chen, Y. et al., *Proximal Tibial Cortex Transverse Distraction Facilitating Healing and Limb Salvage in Severe and Recalcitrant Diabetic Foot Ulcers, Clin Orthop Relat Res* (2020), 478:836-851.

In orthopaedics, devices called external fixators are known for this purpose and are used, for example, in treatments in which a part of the lower leg bone is cut out and new bone tissue is generated by transverse distraction and, in the process, the blood circulation of the surrounding tissue is significantly improved. There is a greatly increased risk of infection, especially because the fixator, which is attached externally to the lower leg, is worn for a long period of time. In addition, the patient's movement and comfort while wearing it are severely restricted, and there is the risk of the fixator being brought out of its predetermined position by external impact or compression forces, which has a negative effect on the healing process. Great effort is needed for caring for the fixator, and there is a risk of infection via the elements (pins), which are arranged both inside and outside the body.

Intramedullary nails for axial distraction of a tubular bone are known, inter alia, from EP 2 990 002. US2002/0165544 and US2017/0143387 disclose an intramedullary nail which is fixed at its ends by means of an expansion mechanism to a tubular bone. The expansion mechanism also comprises a strictly limited radial expansion. In US2002/0165544, sleeves provided with axial slots are arranged for this purpose on the outside of the core of the intramedullary nail and can be crimped in their longitudinal direction by means of an axial screw mechanism and thus extend radially in part similar to a bellows and can bring about clamping at the bone ends. In US2017/0143387, the fastening of the intramedullary nail is brought about by two radially extendable fixing elements, which are deployed from the outer surface of the intramedullary nail by displacement counter to each other and thus achieve a radial expansion uniformly on both sides. The extent of the radial expansion of the fixing elements in US2017/0143387 is limited by the diameter of the intramedullary nail.

A medical device for another surgical use serving to reconstruct a missing tubular bone by callus distraction and which for this purpose comprises an expansion device for bone expansion is disclosed in WO 2013/023898. The expansion device includes successively in the longitudinal direction a plurality of expansion means, which are designed as chambers which are filled by a pump with a medium for the expansion.

In particular, a disadvantage of the prior art devices is that they do not provide a reliable and as gentle as possible a technical solution for transverse distraction. In some known devices, the extent of transverse distraction is essentially limited to the diameter of the intramedullary nail. Some others cannot be adjusted sufficiently precisely or have to be adjusted intraoperatively or frequently invasively.

OBJECT OF THE INVENTION

It is therefore the object of the present invention to provide an intramedullary nail, with the intention being to improve systems which are known from the prior art. In particular, the disadvantages of the prior art are intended to be alleviated or eliminated. The aim is an intramedullary nail which comprises a simple design and allows reliable transverse distraction by means of minimally invasive surgery.

This object is achieved by the subject matter of claim 1. Advantageous embodiments are the subject of the dependent claims.

SUMMARY OF THE INVENTION

One aspect of the invention relates to an intramedullary nail for transverse distraction of a tubular bone, the intramedullary nail comprising an at least partially hollow tube body extending in an axial direction of the intramedullary nail, at least one locking means for locking the tube body in an end portion of the tubular bone, a first inner part and a second inner part, which are each arranged within the tube body so as to be displaceable in the axial direction counter to each other or with each other, a drive within the tube body for axial displacement of the first inner part relative to the second inner part, at least one longitudinal recess in the tube body, and at least one lever mechanism which comprises at least one lever element which is designed to be extended out of, and to be retracted again into, the tube body in the radial direction, wherein the displacement of the first inner part relative to the second inner part causes the at least one lever element to be moved or extended out of the at least one lateral longitudinal recess in the tube body or causes the at least one lever element to be moved or retracted into the at least one lateral longitudinal recess in the tube body.

The extent of the transverse distraction is thus substantially greater than with previous intramedullary nails and is not limited to the diameter of the intramedullary nail. It allows an incremental extension and retraction of the lever mechanism for transverse distraction, without the need for attaching external elements on the patient's body. The displacement of the inner parts relative to each other by means of a drive can preferably be affected by pressure or tension. In addition, the adjustment of the extent of the transverse distraction with the intramedullary nail according to the invention is possible by contact-free energy transmission without intervention. The entire process of transverse distraction is minimally invasive. This provides an active, fully implantable intramedullary nail for transverse distraction, with the implantation and explanation being able to be performed in a minimally invasive manner.

In embodiments, the at least one lever element in a retracted position can be aligned axially with the longitudinal axis of the intramedullary nail and in an extended position can be aligned at an angle of at least 30°, preferably at an angle of at least 45°, even more preferably at an angle of at least 60° and most preferably at an angle of at least 80° with respect to the longitudinal axis of the intramedullary 25 nail. This allows for infinitely variable adjustment of the transverse distraction, which the patient may optionally be able to undertake by themselves. A plurality of lever mechanisms in the intramedullary nail, e.g., two to four, ensure sufficient radial expansion and thus a reliable and uniform transverse distraction in the affected regions.

In preferred embodiments, the drive can be supported axially on the tube body. This allows a reliable displacement of the first inner part with respect to the second inner part.

In advantageous embodiments, the at least one lever element can be configured to be retracted in the longitudinal direction without actuation of the drive during movement of the intramedullary nail. Accordingly, if the drive should fail or the resetting cannot be undertaken by the drive, the intramedullary nail can still be removed as gently as possible because displacement of the two inner parts relative to each other is possible without a drive. This guarantee of optimum failure safety represents a considerable advantage over previous devices.

In a further advantageous embodiment, the second inner part can be integrally formed with the tube body. This allows a design with fewer components. The lever mechanism can then be retracted and folded up with the drive.

In preferred embodiments, the drive can be designed as an electrical, magnetic, electro-magnetic, hydraulic, shape memory based, piezoelectric or pneumatic drive. In particular, such types of drive allow an adjustment of the transverse distraction without invasive intervention and/or without body contact. In addition, for example, with an electromechanical linear drive, very small adjustment steps are possible, which is highly advantageous for callus distraction and the medical healing process. The above-mentioned forms of drive are inexpensive, reliable and permit a simple construction.

In one advantageous embodiment, the drive can comprise a motor, a transmission and preferably a spindle element. Such a design also permits extremely small adjustment steps and provides a reliable and simple construction of the intramedullary nail.

In typical embodiments, the first inner part and the second inner part can have a half-cylinder shape. This results in a simple construction, the components of which can be produced non-problematically. It is also possible that the first inner part and the second inner part have other complementary shapes or cross sections. In a further exemplary embodiment, the intramedullary nail can have a substantially polygonal cross section, so that the first inner part and the second inner part can have corresponding polygonally-matching cross sections or partial cross sections and therefore the two inner parts can be displaced with respect to each other. Other cross-sectional shapes are possible. It is not absolutely necessary for the cross-sectional area of the first inner part to be identical to the cross-sectional area of the second inner part.

In particular embodiments, the at least one lever element can be designed as a rocker arm, which comprises an elongate hole and a joint device, wherein the joint device is rotatably connected on and axially fixed to the first inner part, and wherein the second inner part has a guide element, which is guided in the elongate hole in the rocker arm. Thus, the lever mechanism is constructed comparatively simply, since the rocker arm only has to have an elongate hole and a joint device, wherein the joint device can be a rotary bolt arranged at one end of the rocker arm and a guide bolt is forcibly guided in the elongate hole. A rocker arm may be rectilinear, have rounded edges, and have a conically tapered shape. Other embodiments may have curved or irregularly shaped rocker arms. In further embodiments, a reversal of the operating principle described for rocker arms is also possible, i.e., that, for example, the guiding of the rocker arm is predetermined by a groove or a recess in the first or second inner part. In this way, an embodiment can also be formed with two rocker arms, in which the rocker arms are identical in shape and are adjusted by being synchronously guided during the displacement of the inner parts relative to one other in the manner of a parallelogram.

Further typical embodiments comprise a lever mechanism, wherein the at least one lever element may be designed as a toggle lever. The toggle lever can therefore be guided without an elongate hole and without guide bolts.

In further typical embodiments, the at least one lever element can be designed as a plurality of chain links connected to one another in an articulated manner, wherein one chain link of the plurality of chain links is axially adjacent to the first inner part and another of the plurality of chain links adjoins the second inner part, wherein the displacement of the first inner part relative to the second inner part causes folding and protrusion of at least two chain links through a lateral longitudinal recess in the tube body. This allows radial distraction by means of at least two chain links, but also by means of more than two chain links that are no longer axially aligned in the extended position. The design with a plurality of chain links also provides a stable and simple construction. The guiding of the chain links can be designed in such a way that the end of one chain link protrudes in the radial direction further from the tube body than the end of another chain link. It goes without saying that the chain links do not all have to be the same length. It is also possible for the chain links to have a curved or irregular shape, i.e., they do not necessarily have to be rectilinear in shape. Combinations of rectilinear and irregularly shaped chain links are also possible. The term chain links is also intended to be understood as meaning flexible belts or rigid chains with a plurality of segments. Elements that, in the broadest sense, perform the function of pivot axes when pushing together an assembly of segments are crucial for suitability.

In preferred embodiments, the lever elements or chain links on the side directed outward from the tube body have correspondingly configured surfaces which reinforce the radial distraction effect. The intramedullary nail per se and its components may typically be made of biocompatible material, such as implant steel, other suitable metal alloys, suitable plastics and the like. Suitable manufacturing methods also include 3D printing, for example.

Typical embodiments can be designed in such a manner that one or more plates can be arranged in an articulated manner at the free, outwardly directed ends of the rocker arms or lever elements, said plate(s) covering the longitudinal recess(es) in the retracted state of the lever mechanism and, in the extended state, distributing the radial pressure of the lever mechanism over a flat area. For example, an embodiment with two rocker arms is conceivable, to the end of which a common elongated plate is fastened in each case in an articulated manner, said plate covering a longitudinal recess in the tube body in the retracted state and, in the extended state, being moved completely radially outward, preferably parallel to the outer surface of the tube body.

DETAILED DESCRIPTION OF EXEMPLARY EMBODIMENTS

Figures 1, 2:
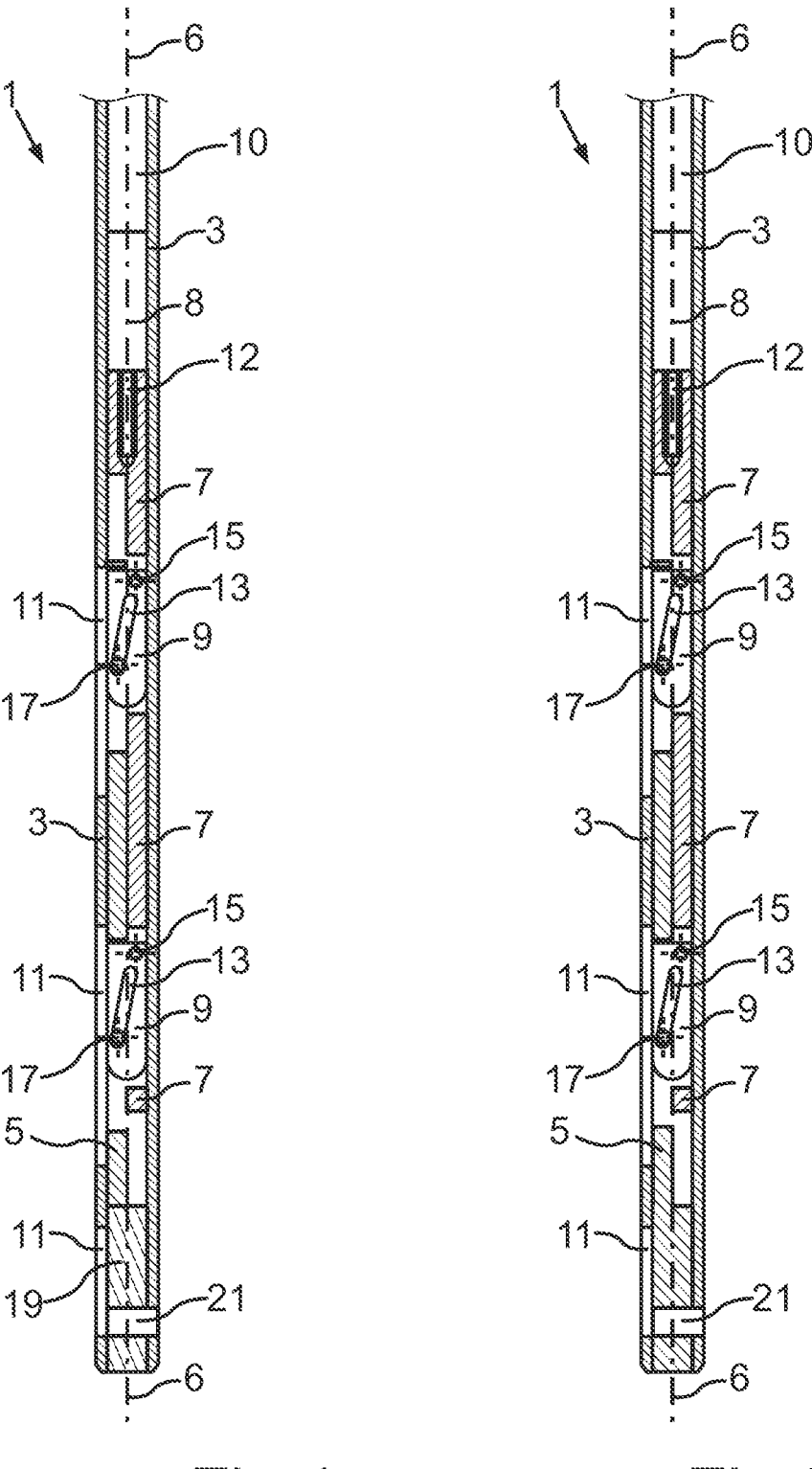
FIG. 1 is a schematic cross-sectional view of a preferred embodiment of the intramedullary nail according to the invention in a first position.
FIG. 2 is a schematic cross-sectional view of a further embodiment of the intramedullary nail according to the invention in a first position.

In the description below, exemplary embodiments are explained with reference to the figures, wherein the same reference symbols are used for identical or similar parts. Under some circumstances, identical or similar parts are not explained again in conjunction with each figure.

The embodiment of the intramedullary nail 1 according to the invention that is described in FIGS. 1-7 comprises a substantially cylindrical hollow tube body 3, in the interior of which a first inner part 5 and a second inner part 7 are accommodated. The first inner part 5 and the second inner part 7 are formed substantially complementarily here as half-cylinders and extend parallel to each other axially, i.e., in the longitudinal direction of the intramedullary nail 1. At its lower end, which is arranged in the lower section in FIG. 1, the intramedullary nail 1 has an end piece 19, which serves for fixing the intramedullary nail 1 to a tubular bone (not shown in FIG. 1). The end piece 19 has a locking means which is attachable to the end portion of a tubular bone, for example with a locking bolt which is guided through corresponding openings in the tube body 3 and through a through hole 21 in the end piece 19. Bolts known from the prior art can be used as locking bolts for fixing intramedullary nails in bones.

The cross section of the intramedullary nail 1 and thus of the basic body 3 is circular in the preferred embodiment shown here. Thus, the first inner part 5 and the second inner part 7 can be formed correspondingly as complementary half-cylinders. The lower end piece 19 also is substantially in the shape of a cylinder. It should be noted that the intramedullary nail 1 may also have a polygonal cross section, for example a triangular, rectangular, square, pentagonal, hexagonal, or octagonal cross section. An elliptical cross section is also possible. The inner parts 5, 7 can then be suitably designed with a corresponding polygonal cross section.

A transmission 8 and, adjacent thereto, a motor 10, which together form a drive, are arranged in the upper portion of the intramedullary nail 1. A spindle 12 which is aligned substantially symmetrically to the longitudinal axis 6 of the tube body 3 is driven by the transmission 8. In the embodiment illustrated here, the spindle 12 comprises an external thread which engages in an internal thread in the second inner part 7 such that a rotation of the spindle brings about a movement of the second inner part 7 in the axial direction. It is also conceivable that the operation is carried out in reverse, e.g. via an axially fixed, driven nut in which a spindle is moved. The power supply and control of the drive can be undertaken via an electrical connection, which is not shown in the figures. In this case, the electrical connection can be connected to a receiver which is arranged subcutaneously in order to permit a contactless control and power supply of the intramedullary nail 1 via a control device which is located outside the patient's body. The power source for the drive can preferably be arranged outside the patient's body; in further embodiments also within the intramedullary nail.

As already mentioned above, the intramedullary nail 1 according to the invention may also have other drives than the electromechanical drive with motor 10 and transmission 8 that is illustrated here.

In principle, the terms "radially" and "axially" in this description refer to the longitudinal axis 6 of the tube body 3.

In the central part, the intramedullary nail 1 of the embodiment shown here has two longitudinal recesses 11, which are aligned substantially parallel to the longitudinal axis 6 and have a width of preferably between 2 mm and 8 mm, even more preferably between 4 mm and 6 mm. Also in the lower section, the tube body 3 has a longitudinal recess 11, which is essentially used for locking and later removal of the intramedullary nail 1 from the tubular bone, as is explained below with reference to FIGS. 6 and 7.

Also, in the middle region level with the longitudinal recesses or elongate holes 11, the interior of the intramedullary nail 1, in the embodiment shown here, has two rocker arms 9, which, when used as intended, form the lever mechanism which is responsible for the transverse distraction. In other words, the rocker arms 9 rotate about an axis of rotation out of the axial position shown in FIG. 1 in such a way that a radial expansion component provides for the transverse distraction, because the rocker arm 9 moves out of the longitudinal recess 11. For this purpose, said or each rocker arm 9 comprises, on the one side (at the top in FIG. 1), a bore aligned transversely to the longitudinal axis 6 as an axis of rotation, through which bore a rotary bolt 15 is guided. The rotary bolt 15 in turn is fixedly arranged on the rocker arm 9 and pivotally connected to the second inner part 7. In a further embodiment, the diameter of the rotary bolt 15 is slightly smaller than that of a bore through the rocker arm 9.

An elongate hole 13 in the rocker arm 9 is formed aligned slightly obliquely to the longitudinal axis 6, wherein a guide element or guide bolt 17 is guided through the elongate hole 13 transversely to the longitudinal extent of the elongate hole 13. The guide bolt 17 is fixedly connected to the first inner part 5.

The lever mechanism with the rocker arm 9 in the embodiment shown here is actuated by the relative displacement of the first inner part 5 relative to the second inner part 7. It is seen in the upper, middle region of FIG. 1 that a cavity is formed between the first inner part 5 and the second inner part 7 in such a way that said cavity is correspondingly reduced in size during an axial movement of the second inner part 7 downward, triggered by the actuation of the motor 10. The second inner part 7 is thus pushed onto the first inner part 5. Since the rotary bolt 15 holds the rocker arm 9 at the foot point on the second inner part 7 and the rocker arm 9 is held in the elongate hole 13 by the forcible guidance of the guide bolt 17, the lower end of the rocker arm 9 in FIG. 1 moves out of the longitudinal recess 11. This tilting movement or pivoting movement about the rotary bolt 15 is limited by the length of the elongate hole 13 and the distance of the second inner part 7 relative to the first inner part 5. The length of the elongate hole 13 and said distance are coordinated with each other such that a maximum pivoting of substantially 90° of the rocker arm 9 with respect to the longitudinal axis 6 is achieved. It is understood that, in the embodiment shown, the dimensions and distances of the two rocker arms 9 and the inner parts 5, 7 are the same, and therefore a synchronous or coordinated movement results. In other embodiments, the lengths of the rocker arms 9 may also differ. Furthermore, it is also possible that the pivot axes of the rotary or guide bolts for each rocker arm 9 deviate slightly from one another. This allows a slightly different tilting direction of different rocker arms 9 to be achieved.

Owing to the infinitely variable adjustment of the drive having the motor 10, transmission 8 and spindle 12 in both directions, a very fine adjustment of the radial expansion, i.e., the transverse distraction, is possible by means of the rocker arm 9. Thus, a patient themselves can adjust the extent of the transverse distraction by corresponding control of the motor 10 from the outside, without requiring the intervention of medical personnel or even a surgeon.

FIG. 2 shows essentially the same intramedullary nail 1 from FIG. 1 in an alternative embodiment, in which only the lower end differs, as follows. Instead of a separate end piece 19 as in the embodiment shown in FIG. 1, the end piece is integrally formed with the first inner part 5 in FIG. 2. This in turn means that the lower end of the intramedullary nail 1 is fastened to the tubular bone by the corresponding locking means through the first inner part 5.

Figure 3:
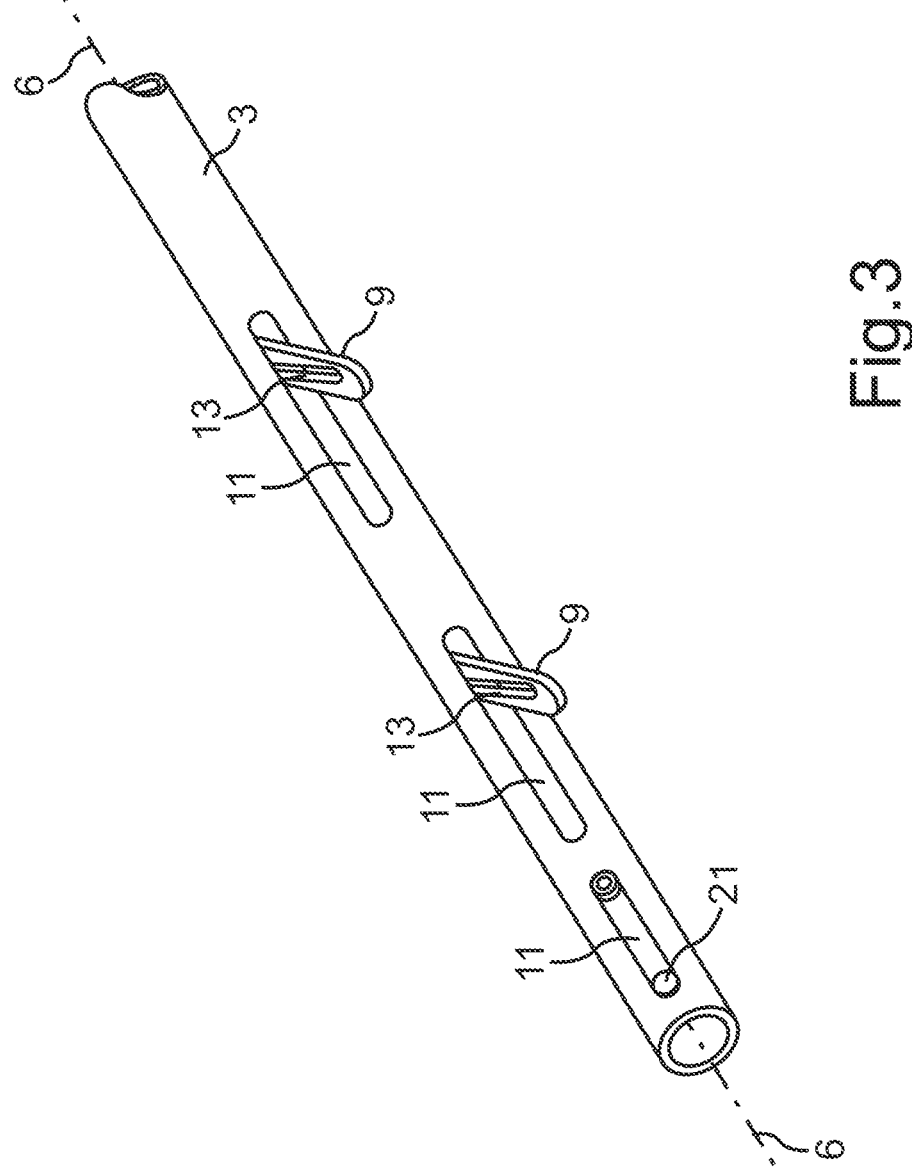
FIG. 3 is a perspective view of a further embodiment of the intramedullary nail according to the invention in a second position.

FIG. 3 shows, in a perspective illustration, the preferred embodiment of the intramedullary nail 1 according to the invention in a second position in which the rocker arms 9 are extended. It can be clearly seen that the amount of radial protrusion of the rocker arms 9 is considerably greater than the diameter of the intramedullary nail 1. This amount can be optimized by suitable selection of the dimensions of the longitudinal recesses 11 and of the rocker arms 9. In addition, it is seen in FIG. 3 that the rocker arm or rocker arms 9 do not have to be fully unfolded or deployed. In principle, any adjustment angle is possible between the angle 0°, i.e., the folded state, and the angle 90°, i.e., the fully unfolded state. This results in a very flexible use of the intramedullary nail for transverse distraction.

Figures 4, 5:
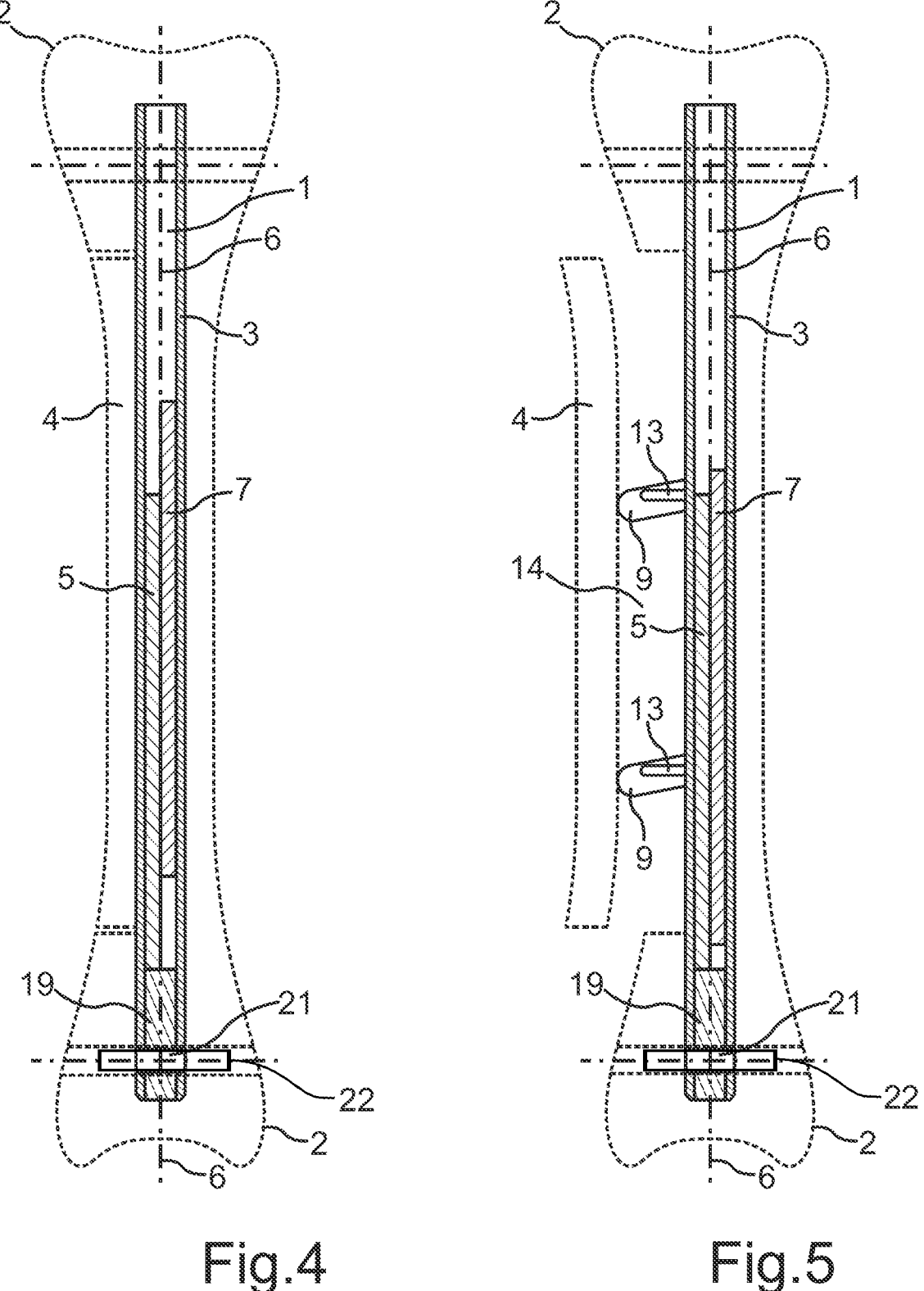
FIG. 4 is a schematic cross-sectional view of the intramedullary nail from FIG. 1 inserted in the first position in a tubular bone.
FIG. 5 is a schematic cross-sectional view of the intramedullary nail from FIG. 1 inserted in the second position in a tubular bone.

FIGS. 4 and 5 show a schematic cross-sectional view of the intramedullary nail 1 from FIG. 1 inserted in the first and second position in a tubular bone 2, here a lower leg bone. The tubular bone 2 is shown here in dashed lines and is expressly not part of the present invention. The intramedullary nail 1 is fixed axially and in a torsion-proof manner in the lower and upper portion of the tubular bone 2 via corresponding locking means through openings 21. This type of fixation by means of minimally invasive intervention is known in the prior art. To prepare the transverse distraction, an elongate portion 4 in the central region of the tubular bone 2 is removed, i.e., for example, sawed out at its circumference with a fine bone saw. The intramedullary nail 1 lies against the elongate portion 4 of the tubular bone 2 over the entire length thereof in the position of FIG. 4. This represents the starting position before the transverse distraction, i.e., the drive within the intramedullary nail 1 has not yet been actuated. The first inner part 5 has not yet been displaced with respect to the second inner part 7, and instead there is still the original axial offset in between.

FIG. 5 shows the state after actuation of the drive and thus after or during the transverse distraction. The first inner part 5 and the second inner part 7 are displaced closer into each other by the drive (not shown in FIGS. 4 and 5), wherein the rocker arms 9 have moved from their starting position aligned in the axial direction (FIG. 4) into the unfolded or extended distraction position. In the embodiment illustrated here, the rocker arms 9 have each moved radially outward by the same amount through the longitudinal recesses 11. In this case, they have come into abutment laterally against the elongate portion 4 of the tubular bone 2 and have moved said portion transversely outward by a distraction distance such that a distraction space 14 results between the outer surface of the tube body 3 and the inner surface of the elongate portion 4. At this point it should be noted that the illustration selected here is schematic.

Figures 6, 7:
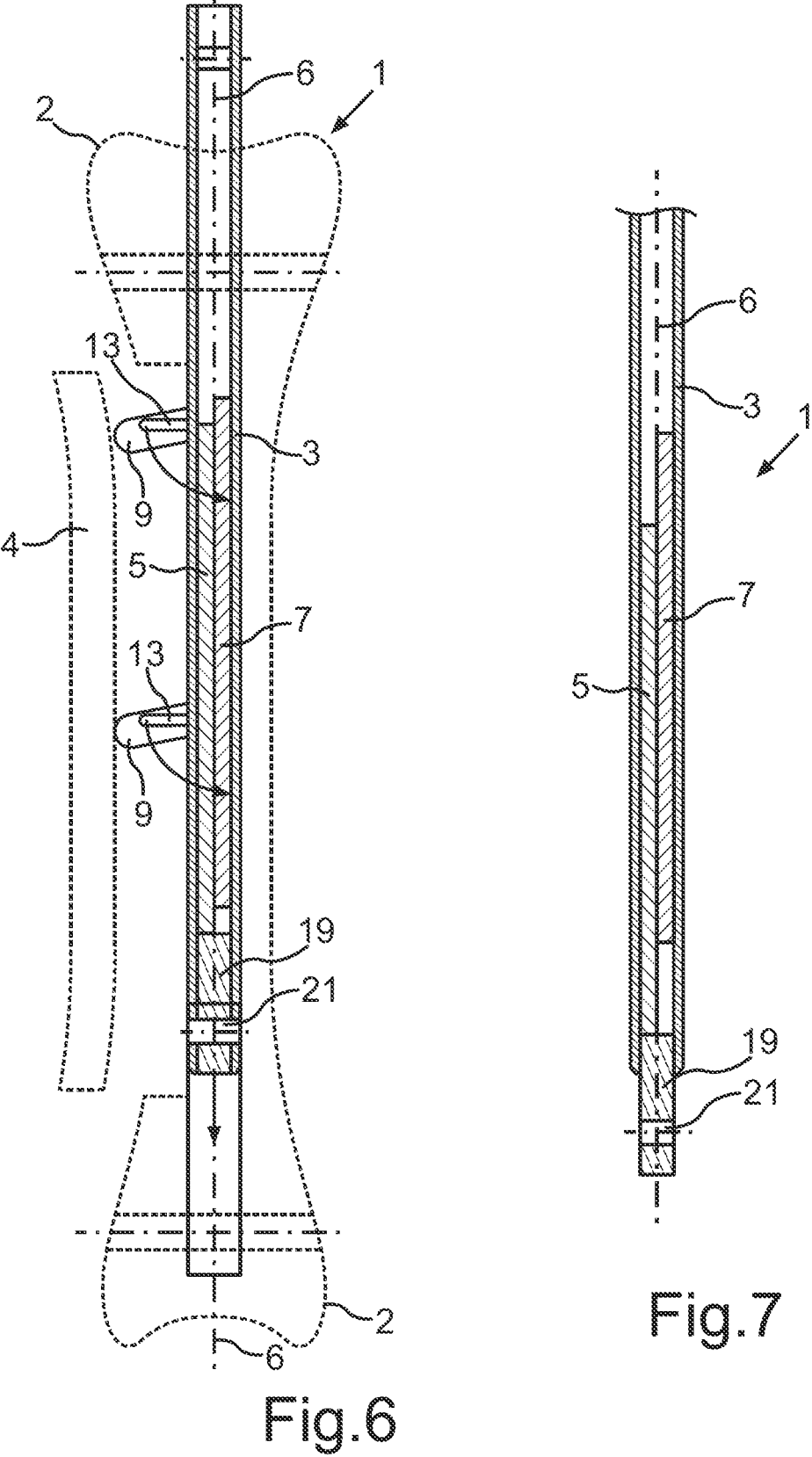
FIG. 6 is a schematic cross-sectional view of the intramedullary nail from FIG. 1 after leaving the second position.
FIG. 7 is a schematic cross-sectional view of the intramedullary nail from FIG. 1 in an extended position.

FIG. 6 shows a third position of the intramedullary nail 1 of the embodiment from FIG. 1 in the tubular bone 2, which is a particular position: the intramedullary nail 1 is removed in this position from the tubular bone 2, namely axially substantially along the longitudinal axis 6. Before the intramedullary nail 1 can be removed, the corresponding locking means at the upper or lower end of the tubular bone has to be loosened and removed so that no further axial fixation is available. If the intramedullary nail 1 is now pulled further upward, e.g., by a surgeon, the rocker arms 9 are initially still extended, i.e., in their distraction position. However, as soon as the upper rocker arm 9 lies against the upper portion of the tubular bone 2, that is, at the end of the elongate portion 4, a further movement of the intramedullary nail 1 upward causes the rocker arm 9 to fold in. This is possible because of the guidance in the elongate hole 13. At the same time, the forcible guidance in the elongate hole 13 also causes the first inner part 5 to move apart relative to the second inner part 7, because the rocker arm 9 is fixed at its foot on the second inner part 7 via the rotary bolt 15. Consequently, the first inner part 5 moves downward relative to the second inner part 7 and also to the tube body 3. This in turn causes displacement of the end piece 19 within tube body 3 through the first inner part 5.

This makes it possible for both rocker arms 9 to fully move back into the tube body 3 and fold in. In particular, the end piece 19 is pushed out of the tube body 3 downward. This can be done by the fact that, after release of the locking means through the through opening 21 in the end piece 19, there is no longer any axial fixation on the bone and, by pulling of the entire intramedullary nail 1 upward, the end piece 19 can move into the space which has become free in the tubular bone 2. For medical use or for the patient, this means that, even without actuation of the drive or in the event of failure or a malfunction of the drive, a residue-free, substantially problem-free removal of the intramedullary nail 1 can be undertaken with minimal surgical intervention. FIG. 7 shows schematically the removed intramedullary nail 1, in which the rocker arms 9 are folded in and the end piece 19 protrudes downward out of the tube body 3.

Figure 8:
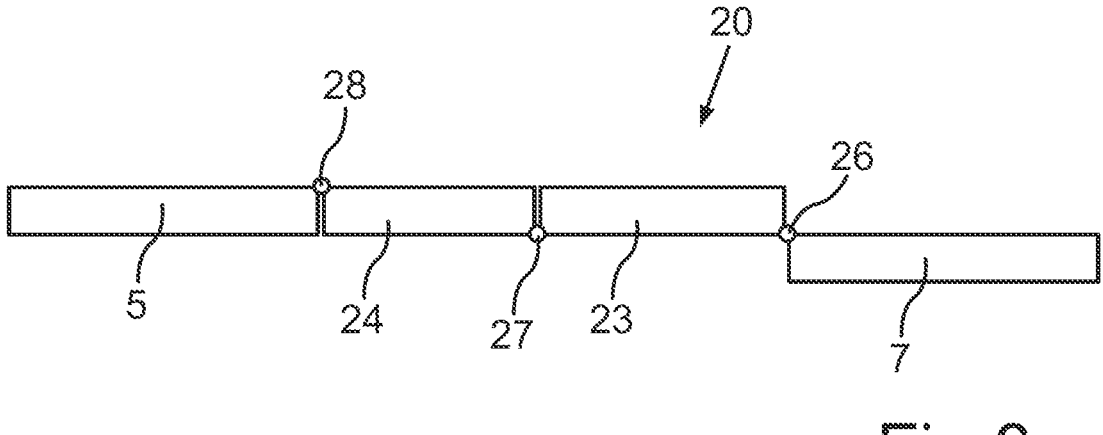
FIG. 8 is a schematic illustration of a lever mechanism according to another embodiment in a first position.
Figure 9:
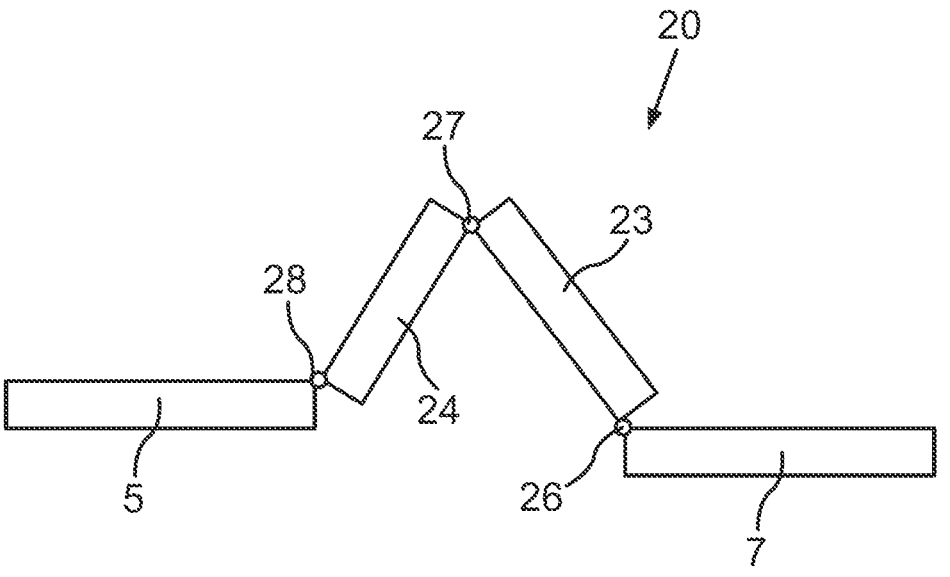
FIG. 9 is a schematic illustration of a lever mechanism from FIG. 8 in a second position.

FIGS. 8 and 9 schematically illustrate an alternative embodiment for the lever mechanism of the intramedullary nail 1 according to the invention. FIG. 8 shows the lever mechanism 20 in the retracted position, i.e. the manner in which it is axially aligned within the tube body 3 (not shown). A first lever element 23 is coupled to the second inner part 7 via a first pivot axis 26, the first pivot axis 26 being aligned transversely to the longitudinal axis 6 of the tube body 3. A second lever element 24 is coupled on the distal side of the second inner part 7 of the first lever element 23 via a second pivot axis 27, the second pivot axis 27 being aligned parallel to the first pivot axis 26. The second lever element 24 is in turn connected in an articulated manner to the first inner part 5 via a third pivot axis 28, wherein the third pivot axis 28 is also aligned parallel to the first pivot axis 26. The lever mechanism shown in FIGS. 8 and 9 is a link chain or rigid chain here. Such mechanisms can also be implemented with segmented belts, which also function in tension and not only with thrust. Owing to the relative displacement of the two inner parts, a function in tension can also be realized in addition to the thrust principle shown in the figures.

If the drive of the intramedullary nail 1, as described above for example, then moves the second inner part 7 in the direction of the first inner part 5, which is axially fixed with respect to the tube body 3, the first lever element 23 and the second lever element 24, as shown in FIG. 9, move out of the axial alignment along the longitudinal axis 6 into a tilting position. In this case, the two lever elements 23, 24 move out through the longitudinal recess 11 in the tube body 3 and the lever mechanism 20 transversely to the longitudinal axis 6 such that said lever mechanism contributes to the transverse distraction. The principle of the lever mechanism 20 shown in FIGS. 8 and 9 corresponds to a chain link arrangement, wherein the number of lever elements is not limited to two as shown in the illustration. There is a multiplicity of possible designs for such a lever mechanism 20. For example, the lever elements do not necessarily have to be rectilinear. The decisive factor is that the relative displacement of the first inner part 5 with respect to the second inner part 7 results in folding of the lever elements, which then move out of the longitudinal recess in the tube body in the axial direction. In addition, a movement of the inner parts 5, 7 in the opposite direction is intended to bring about folding or retraction of the lever mechanism 20.

Similar to the principle shown in FIGS. 8 and 9, a toggle lever mechanism is also conceivable, in which one end of a first lever element is fastened in an articulated manner in the central region of a second lever element.

For convenience in interpreting the figures, the following list of reference numbers is provided:

| |
|---|
| 1 - intramedullary nail |
| 2 - tubular bone |
| 3 - tube body |
| 4 - bone segment/elongate portion |
| 5 - first inner part |
| 6 - longitudinal axis |
| 7 - second inner part |
| 8 - transmission |
| 9 - rocker arm |
| 10 - motor |
| 11 - longitudinal recess |
| 12 - spindle |
| 13 - elongate hole |
| 14 - distraction space |
| 15 - rotary bolt |
| 17 - guide element |
| 19 - end piece |
| 20 - lever mechanism |
| 21 - through opening |
| 23 - first lever element |
| 24 - second lever element |
| 26 - first pivot axis |
| 27 - second pivot axis |
| 28 - third pivot axis |

The invention claimed is:

1. An intramedullary nail for transverse distraction of a tubular bone wherein the intramedullary nail is configured to displace a cutout bone portion of tubular bone in a radial direction, the cutout bone portion having an inner surface, the intramedullary nail comprising: an at least partially hollow tube body extending in an axial direction of the intramedullary nail; at least one insertable anchoring device for locking the tube body in an end portion of the tubular bone; a first inner part and a second inner part each arranged within the tube body to be displaceable in the axial direction counter to or with each other; a drive within the tube body for axial displacement of the first inner part relative to the second inner part; at least one longitudinal recess in the tube body; and at least one lever mechanism which includes at least one lever element which is configured to be extended out of, and to be retracted again into, the tube body in a radial direction, the at least one lever element, when extended, is longer than a distance from bone center to the inner surface of the bone and of sufficient length to radially displace the cutout bone portion inner surface by a distraction distance, wherein (a) the displacement of the first inner part relative to the second inner part causes the at least one lever element to be moved or extended out of the at least one longitudinal recess in the tube body or causes the at least one lever element to be moved or retracted into the at least one longitudinal recess in the tube body, and (b) the at least one lever mechanism is supported against the tube body such that, in use, the cutout bone portion is displaced in a radial direction away from the tube body.

2. The intramedullary nail of claim 1 having a longitudinal axis and wherein the at least one lever element in a retracted position is aligned axially with the longitudinal axis and in an extended position is aligned at an angle of at least 30° with respect to the longitudinal axis.

3. The intramedullary nail of claim 2 wherein the at least one lever element in an extended position is aligned at an angle of at least 45° with respect to the longitudinal axis.

4. The intramedullary nail of claim 2 wherein the at least one lever element in an extended position is aligned at an angle of at least 60° with respect to the longitudinal axis.

5. The intramedullary nail of claim 2 wherein the at least one lever element in an extended position is aligned at an angle of at least 80° with respect to the longitudinal axis.

6. The intramedullary nail of claim 1 wherein the drive is supported axially on the tube body.

7. The intramedullary nail of claim 1 having a longitudinal axis and wherein the at least one lever element is designed to be retracted in a longitudinal direction without actuation of the drive during movement of the intramedullary nail.

8. The intramedullary nail of claim 1 wherein the second inner part is integrally formed with the tube body.

9. The intramedullary nail of claim 1 wherein the drive is configured as a drive selected from the group consisting of electrical, magnetic, electro-magnetic, hydraulic, shape-memory-based, piezoelectric, and pneumatic drives.

10. The intramedullary nail of claim 1 wherein the drive has a motor, a transmission, and a spindle element.

11. The intramedullary nail of claim 1 wherein the first inner part and the second inner part each have a half-cylinder shape.

12. The intramedullary nail of claim 1 wherein (a) the at least one lever element is configured as a rocker arm having an elongate hole and a joint device, (b) the joint device is rotatably connected on and axially fixed to the first inner part, and (c) the second inner part has a guide element which is guided in the elongate hole in the rocker arm.

13. The intramedullary nail of claim 1 wherein (a) the at least one lever element is configured as a plurality of chain links connected to one another in an articulated manner, (b)

one chain link of the plurality of chain links is axially adjacent to the first inner part and another of the plurality of chain links adjoins the second inner part, and (c) the displacement of the first inner part relative to the second inner part causes folding and protrusion of at least two chain links through the lateral longitudinal recess in the tube body.

* * * * *